United States Patent [19]

Suzuki et al.

[11] 4,317,710
[45] Mar. 2, 1982

[54] COLORING-DECOLORING-DRYING APPARATUS FOR ELECTROPHORESIS

[75] Inventors: Hideo Suzuki, Tokyo; Ryo Fujimori, Hachiouji, both of Japan

[73] Assignee: Olympus Optical Co., Ltd., Tokyo, Japan

[21] Appl. No.: 197,742

[22] Filed: Oct. 16, 1980

[30] Foreign Application Priority Data

Oct. 18, 1979 [JP] Japan ............................ 54-134625

[51] Int. Cl.³ ............................................. G01N 27/26
[52] U.S. Cl. ............................ 204/299 R; 204/180 R; 204/180 G; 204/300 R
[58] Field of Search ............... 204/300 EC, 212, 299, 204/180 R, 180 S, 180 G, 206; 239/302, 290, 291, 292; 34/43, 44

[56] References Cited

U.S. PATENT DOCUMENTS

| | | | |
|---|---|---|---|
| 2,820,752 | 1/1958 | Heller | 204/300 X |
| 3,020,224 | 2/1962 | Blank et al. | 204/300 X |
| 3,502,563 | 3/1970 | Schmidt | 204/300 X |
| 3,835,005 | 9/1974 | Dudley et al. | 204/300 X |
| 3,930,880 | 1/1976 | Hoefer | 204/280 G X |
| 4,084,541 | 4/1978 | Ito | 204/180 G X |
| 4,115,234 | 9/1978 | Anselrode | 204/299 R X |

Primary Examiner—Arthur C. Prescott
Attorney, Agent, or Firm—Cushman, Darby & Cushman

[57] ABSTRACT

A coloring-decoloring-drying apparatus for electrophoresis comprising a coloring-decoloring container having an opening used for inserting a carrier, pouring coloring and decoloring liquid agents and other purpose and rollers arranged in the vicinity of the opening of said coloring-decoloring container, and adapted in such a manner that a carrier sent from an electrophoretic apparatus is inserted into said coloring-decoloring container by operating said rollers, the rear end of the carrier is held between said rollers, coloring and decoloring liquid agents are poured into said container for coloring and decoloring said carrier while it is held in the condition described above, and then the carrier is dried by blowing hot air through said opening. Said coloring-decoloring-drying apparatus for electrophoresis is so designed as to be capable to performing coloring, decoloring and drying of a carrier without injuring or tearing the carrier.

9 Claims, 5 Drawing Figures

COLORING-DECOLORING-DRYING APPARATUS FOR ELECTROPHORESIS

BACKGROUND OF THE INVENTION (a) Field of the Invention

The present invention relates to an apparatus for coloring, decoloring and drying sample carriers in electrophoretic systems.

(b) Description of the Prior Art

The electrophoresis is utilized for measuring proteins contained in blood serum in clinical inspection laboratories, etc. of hospitals and medical institutes. For the electrophoresis, blood serum to be analyzed is applied onto a carrier which is made of cellulose acetate or the similar material and then the carrier is electrically energized for developing fractionated patterns of the blood serum. The carrier is colored with a coloring liquid agent and, after the area other than the blood serum is decolored, the sample is subjected to colorimetry for quantitative determination. Conventionally, various processes of this analysis were manually carried out with low efficiency. Further, analysis by the electrophoresis required highly delicate skill and the conventional electrophoretic system had a defect that analytical results were different depending on individual analysts' measuring skills. In view of such circumstances, there have hitherto been developed automatic electrophoretic systems which can automatically carry out the processes of the electrophoresis for the purpose of enhancing measuring efficiency and eliminating analytical variations due to difference in measuring skills depending on individual analysis. As an apparatus to carry out the coloring, decoloring and drying processes out of the various steps of the electrophoresis, there has been known an apparatus disclosed by Japanese published unexamined Utility Model No. 158694/54. This coloring-decoloring-drying apparatus is designed in such a manner that a carrier is bonded onto circumference of a drum, rotated therewith so as to pass through a liquid container filled with a coloring or decoloring liquid agent for coloring and decoloring said carrier and, after the carrier is decolored, it is dried by exposing it to hot air blast or the similar means. An outline of this coloring-decoloring-drying apparatus will be described with reference to FIG. 1. A carrier 1 onto which fractionated patterns of a sample have been developed in an electrophoretic apparatus (not shown) is fed between a roller 2 and a drum 3 by an adequate means. The carrier which is soaked with a buffer solution is thus bonded onto the drum 3 consecutively from the leading end of said carrier. When the leading end of the carrier has passed just beyond another roller 4, rotation of the drum 3 is stopped so that the carrier 1 is held in the condition where it is bonded onto the outer circumference of the drum 3 while being held with both the rollers 2 and 4. In this condition, the drum 3 is rotated together with the rollers 2 and 4 so that the carrier 1 is rotated while it is bonded onto the drum 3 and held with the rollers 2 and 4. A liquid container 5 is filled with a coloring liquid agent, and therefore the carrier is colored since it passes through the liquid agent during its rotation. The carrier is decolored in the similar way when the container is filled with a decoloring liquid agent instead of the coloring liquid agent. After the carrier has been colored and decolored as described above, it is dried with a hot air blast supplied from a blower port (not shown), and then the drum 3 only is rotated to feed the carrier 1 to the next process. The coloring-decoloring-drying apparatus described above has a surface 3a having a curvature lower than the imaginary circular circumference of the drum 3 which serves for preventing the carrier 1 from being torn due to contraction at the drying process. Since degree of the contraction is different depending on materials of the carrier, curvature of the surface should ideally be varied depending on contraction degree of the carrier. Further, when the carrier has a short length, it is required to use a drum having a small diameter. In such a case, the carrier bonded onto the drum is held in a strongly curved condition and such a curved form remains at the subsequent processes, thereby causing inconvenience at the processes after the coloring and decoloring. Moreover, the drum type of apparatus shown in FIG. 1 has a drawback in that it has a very complicated mechanism and requires a large number of parts.

SUMMARY OF THE INVENTION

A general object of the present invention is to provide a coloring-decoloring-drying apparatus for electrophoresis comprising a coloring-decoloring container having an opening for inserting and sending out the carrier, and rollers arranged in the vicinity of the opening of said coloring-decoloring container, said apparatus being adapted in such a manner that the carrier is fed by said rollers into said coloring-decoloring container, then suspended in said container in a condition where trailing end of the carrier is held between said rollers, colored and decolored by pouring coloring and decoloring liquid agents into said container, and then dried by blowing a hot air blast into said container.

DETAILED DESCRIPTION OF THE PREFERRED EMBODIMENT

Now, the present invention will be described more in a more detailed manner with reference to the preferred embodiment illustrated in the accompanying drawings.

Figure 2:
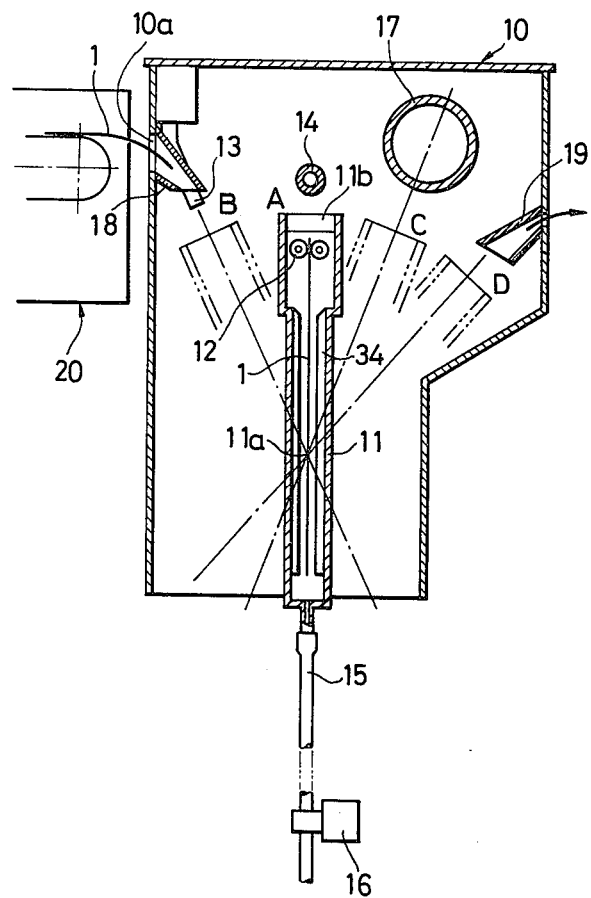
FIG. 2 shows a sectional view illustrating construction of the coloring-decoloring-drying apparatus according to the present invention.

In FIG. 2, the reference numeral 10 represents a main casing of the coloring-decoloring-drying apparatus according to the present invention, the reference numeral 11 designates a coloring-decoloring container which is arranged rotatably around an axis 11a in the main casing 10 and the reference numeral 12 denotes rollers which are arranged in the coloring-decoloring container and used for feeding the carrier 1 into the coloring-decoloring container 11 and holding said carrier in said container. The reference numeral 13 represents a coloring liquid agent nozzle, the reference numeral 14 designates a decoloring liquid agent nozzle, the reference numeral 15 denotes a drain hose connected to a drain port formed at the lower end of the coloring-decoloring container, the reference numeral 16 represents a pinch valve, the reference numeral 17 designates a drying air pipe and the reference numerals 18 and 19 denote guides. In addition, feeding of the carrier can be made more certain by holding the follower roller of the rollers 12 so as to be slightly movable relative to the container 11 and pressing it onto the driver roller with a spring or the similar means.

In this coloring-decoloring-drying apparatus having such a construction as described above, the coloring-decoloring container 11 is turned counterclockwise from the position shown in the drawing (indicated by the reference symbol A) to the position indicated by the symbol B. In this condition, the carrier 1 which has been subjected to electrophoresis in an electrophoretic apparatus 20 is sent out of the electrophoretic apparatus 20 and fed into the main casing 10. The carrier is directed by the guide 18 toward coloring-decoloring container 11 kept at the position B, and inserted deep into the container by the rollers 12 arranged in the coloring-decoloring container. When the rear end of the carrier reaches the vicinity of the rollers 12, these rollers are stopped so that the carrier is kept in suspended condition in the coloring-decoloring container 11 with one end of said carrier held between both the rollers. At this state, a coloring liquid agent is poured through the coloring liquid agent nozzle 13 into the coloring-decoloring container 11 until it is filled with the coloring liquid agent. Therefore, the carrier is dipped into the coloring liquid agent and colored while being kept in the container 11. Then, the coloring-decoloring container 11 is returned to position A and kept in this position for a definite time while the carrier is dipped in the coloring liquid agent. After the carrier has been colored sufficiently, the pinch valve 16 is opened to discharge the coloring liquid agent from the coloring-decoloring container through the drain hose 15. After the pinch valve 16 is closed, a decoloring liquid agent is poured into the coloring-decoloring container 11 through the decoloring liquid agent nozzle 14 for decoloring the carrier. After a predetermined time has elapsed, the pinch valve 16 is opened once again for discharging the decoloring liquid agent from the coloring-decoloring container 11 through the drain hose 15. This decoloring process is repeated several times until the carrier is decolored completely. After completing the decoloring process, the coloring-decoloring container 11 is turned clockwise around the axis 11a and stopped at the drying position (indicated by the reference symbol C) at which the upper opening 11b is located under the drying air pipe 17. With the coloring-decoloring container 11 kept in this position, hot air blast is supplied from the drying air pipe 11 to dry the carrier. After the carrier has been dried completely, the coloring-decoloring container 11 is turned further clockwise until it reaches the carrier sending out position (indicated by the reference symbol D). With the container 11 kept in this position, rollers 12 are rotated to send the carrier 1 through the guide 19 and sent out port 10b to the next process.

Figure 1:
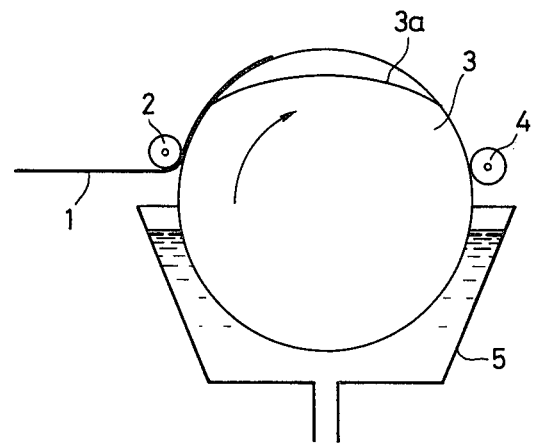
FIG. 1 shows a sectional view schematically illustrating outline of the conventional coloring-decoloring apparatus.
Figure 3:
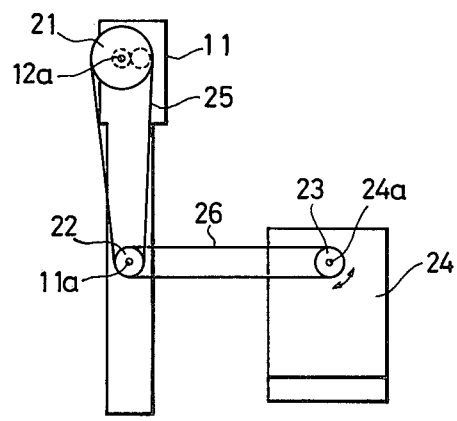
FIG. 3 shows a side view illustrating a mechanism for rotating the rollers in the coloring-decoloring-drying apparatus according to the present invention.
Figure 4:
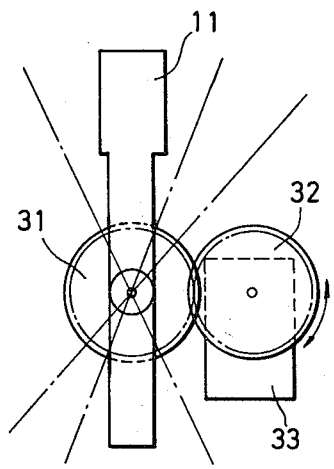
FIG. 4 shows a side view illustrating a mechanism for turning the coloring-decoloring container in the coloring-decoloring-drying apparatus according to the present invention.
Figure 5:
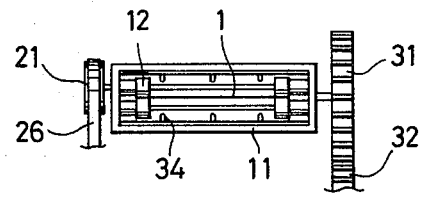
FIG. 5 shows a plan view illustrating construction of said coloring decoloring container.

Now, the mechanisms for turning the coloring-decoloring container and rotating the rollers of the coloring-decoloring-drying apparatus will be described. FIG. 3 shows a side view illustrating construction of the mechanism for driving the rollers 12 arranged in the coloring-decoloring container 11. The reference numeral 21 represents a pulley fixed to the shaft 12a of one of the rollers 12, the reference numeral 22 designates a second pulley attached to the turning shaft 11a of the coloring-decoloring container 11, the reference numeral 23 denotes a third pulley attached to a rotating shaft 24a of a motor 24 for driving the rollers, and the reference numerals 25 and 26 represent belts which are passing around a pair of pulleys 21 and 22 and another pair of pulleys 22 and 23 respectively. When the motor 24 is rotated in either direction in this mechanism, the carrier 1 is fed into or sent out of the container 11 by operating the pulleys 22, 23, etc. as well as belts 25 and 26. FIG. 4 shows a side view illustrating construction of the mechanism for turning the coloring-decoloring container 11. In FIG. 4, the reference numeral 31 represents a gear fixed to the returning shaft 11a (on the surface located on the opposite side of the pulley 21 shown in FIG. 3) of the coloring-decoloring container 11, the reference numeral 32 designates another gear which is in mesh with the gear 31, and the reference numeral 33 denotes a motor for turning the coloring-decoloring container. When the motor 33 is rotated in either direction in this mechanism, the coloring-decoloring container 11 is turned clockwise or counterclockwise. Though the mechanism for rotating the rollers and the mechanism for turning the coloring-decoloring container are illustrated separately in FIG. 3 and FIG. 4 respectively, these mechanisms are actually arranged on both the right and left sides of the coloring-decoloring container as shown in FIG. 5. The reference numeral 34 represents members which are arranged for preventing the carrier fed into the container from adhering to the inside wall thereof.

As is understood from the foregoing descriptions, the coloring-decoloring-drying apparatus according to the present invention permits coloring and decoloring the carrier while holding it in suspended condition with one end thereof held between the rollers, and is free from the defect of forming a curved shape on the carrier, or injuring or tearing the carrier due to contraction in the drying process. Further, the coloring-decoloring-drying apparatus according to the present invention has a simple construction consisting only of the coloring-decoloring container, rollers arranged therein and so on.

Though the present invention has been described with reference to the embodiment in which the coloring-decoloring container is turned for positioning at the carrier insertion position, coloring-decoloring position, drying position and carrier sending out position, the present invention is not limited to this embodiment only. For example, the coloring-decoloring-drying apparatus according to the present invention may be designed with the coloring-decoloring container kept fixed and the coloring liquid agent nozzle and others shiftable over the opening of said container.

We claim:
1. A carrier coloring-decoloring-drying apparatus for electrophoresis, comprising:
a coloring-decoloring container having opening means used for insertion of a carrier of predetermined length into said container, for pouring coloring and decoloring liquid agents into said container, and a drain port;
a pair of rollers arranged inside said coloring-decoloring container and used for inserting and sending out said carrier;
said apparatus being so arranged that when the carrier having been subjected to electrophoresis is fed into said coloring-decoloring container through said opening means by rotating said rollers in feeding contact with the carrier, said carrier is kept in suspended condition with its rear end held between said rollers while a coloring liquid agent is poured into said container through said opening means to color said carrier, said coloring liquid agent is then discharged from said container through said drain port, a decoloring liquid agent is then poured into said container through said opening means to decolor said carrier, said decoloring liquid agent is then discharged from said container through said drain portion, and then said carrier is dried by blowing a hot air blast through said opening means.

2. A carrier coloring-decoloring-drying apparatus for electrophoresis according to claim 1 wherein said rollers are arranged in the vicinity of said opening means of said coloring-decoloring container.

3. A carrier coloring-decoloring-drying apparatus for an electrophoretic system according to claim 1, further including:
a common main casing, which houses said container, said rollers, said nozzle means for liquid coloring agent, said nozzle means for liquid decoloring agent and said means for delivering a drying blast of air;
said common main casing further including an inlet opening into the common main casing, through which the carrier may be guided into said rollers and an outlet opening from the common main casing, through which said carrier may be expelled by said rollers.

4. A carrier coloring-decoloring-drying apparatus for an electrophoretic system according to claim 3, wherein:
said inlet opening, said nozzle means for delivering liquid coloring agent, said nozzle means for delivering liquid decoloring agent, said means for delivering a drying blast of air, and said outlet opening all are arranged in sequence in an arc; and
said sequencing means comprises means movably mounting said container and means for moving said container for sequentially juxtaposing said opening of said container with said inlet opening, said nozzle means for delivering liquid coloring agent, said nozzle means for delivering liquid decoloring agent, said means for delivering a drying blast of air, and said outlet opening.

5. A carrier coloring-decoloring-drying apparatus for electrophorsis, comprising:
a coloring-decoloring container having opening means used for insertion of a carrier of predetermined length into said container, for pouring coloring and decoloring liquid agents into said container, and a drain port;
a pair of rollers arranged inside said coloring-decoloring container and used for inserting and sending out said carrier;
said apparatus being so arranged that when the carrier having been subject to electrophorsis is fed into said coloring-decoloring container through said opening means by rotating said rollers in feeding contact with the carrier, said carrier is kept in suspending condition with its rear end held between said rollers while a coloring liquid agent is poured into said container through said opening means to color said carrier, said coloring liquid agent is then discharged from said container through said drain port, a decoloring liquid agent is then poured into said container through said opening means to decolor said carrier, said decoloring liquid agent is then discharged from said container through said drain port, and then said carrier is dried by blowing a hot air blast through said opening means;
a coloring liquid agent nozzle, a decoloring liquid agent nozzle and a hot air blowing port being further arranged in the vicinity of said opening means of said coloring-decoloring container, said coloring-decoloring container being mounted so as to be rotatable around a point so as to shift said opening means thereof, and means permitting said coloring-decoloring container to be turned consecutively to position its opening under said coloring liquid agent nozzle, said decoloring liquid agent nozzle and said hot air blowing port respectively for performing pouring of a coloring liquid agent, decoloring liquid agent and blowing of hot air.

6. A carrier coloring-decoloring-drying apparatus for electrophoresis, comprising:
a coloring-decoloring container having opening means used for insertion of a carrier of predetermined length into said container, for pouring coloring and decoloring liquid agents into said container, and a drain port;
a pair of rollers arranged inside said coloring-decoloring container and used for inserting and sending out said carrier;
said apparatus being so arranged that when the carrier having been subjected to electrophoresis is fed into said coloring-decoloring container through said opening means by rotating said rollers in feeding contact with the carrier, said carrier is kept in suspended condition with its rear end held between said rollers while a coloring liquid agent is poured into said container through said opening means to color said carrier, and coloring liquid agent is then discharged from said container through said drain port, a decoloring liquid agent is then poured into said container through said opening means to decolor said carrier, said decoloring liquid agent is then discharged from said container through said drain port, and then said carrier is dried by blowing a hot air blast through said opening means;
a mechanism for rotating said rollers and another mechanism for turning said coloring-decoloring container, and means for driving said mechanism for rotating the rollers and said mechanism for turning the coloring-decoloring container from a single driving source.

7. A carrier coloring-decoloring-drying apparatus for electrophoresis according to claim 6 wherein said mechanism for rotating said rollers is arranged on one side of said coloring-decoloring container and said mechanism for turning said coloring-decoloring container is arranged on the other side of said coloring-decoloring container.

8. A carrier coloring-decoloring-drying apparatus for electrophoresis, comprising:
a coloring-decoloring container having opening means used for insertion of a carrier of predetermined length into said container, for pouring coloring and decoloring liquid agents into said container, and a drain port;
a pair of rollers arranged inside said coloring-decoloring container and used for inserting and sending out said carrier;
said apparatus being so arranged that when the carrier having been subjected to electrophorsis is fed into said coloring-decoloring container through said opening means by rotating said rollers in feeding contact with the carrier, said carrier is kept in suspended condition with its rear end held between said rollers while a coloring liquid agent is poured into said container through said opening means to color said carrier, said coloring liquid agent is then discharged from said container through said drain port, a decoloring liquid agent is then poured into said container through said opening means to decolor said carrier, said decoloring liquid agent is then discharged from said container through said drain port, and then said carrier is dried by blowing a hot air blast through said opening means;

a coloring liquid agent nozzle, a decoloring liquid agent nozzle and a hot air blowing nozzle port which are movably arranged respectively in the vicinity of the opening means of said coloring-decoloring container, and adapted in such a manner that said coloring liquid agent nozzle is moved over said opening means for pouring a coloring liquid agent into said container, said decoloring liquid agent nozzle is moved over said opening means for pouring a decoloring liquid agent into said container and said hot air blowing port is moved over said opening means for blowing a hot air blast into said container.

9. A carrier coloring-decoloring drying apparatus for an electrophoretic system, comprising:

a generally vertically oriented coloring-decoloring-drying container having an upper end opening;

a pair of rollers juxtaposed with said opening and adapted to accept and feed an electrophoresis sample carrier of determinate length into said container through said upper end opening, to hold said carrier hangingly suspended in said container by maintaining gripping contact with a trailing end portion of said carrier while said carrier is being subjected to coloring, decoloring and drying in said container, and then to feed said carrier back out of said container through said opening;

nozzle means for liquid coloring agent, nozzle means for liquid decoloring agent and means for delivering a drying blast of air;

sequencing means for sequentially delivering liquid coloring agent from said nozzle means for liquid coloring agent into said container through said opening for coloring said carrier while said carrier is hangingly suspending in said container by said rolls, for delivering liquid decoloring agent into said container through said opening for decoloring said carrier while said carrier is hangingly suspended in said container by said rolls, and for air-drying said carrier by delivering a blast of air into said container through said opening from said means for delivering a drying blast of air while said carrier is hangingly suspended in said container by said rolls; and means for draining spent liquid coloring agent from said container before decoloring said carrier and for draining spent liquid decoloring agent from said container after decoloring said carrier.

* * * * *